(12) United States Patent
Cowe

(10) Patent No.: US 9,956,348 B2
(45) Date of Patent: May 1, 2018

(54) DOSING MECHANISM

(71) Applicant: OWEN MUMFORD LIMITED, Oxfordshire (GB)

(72) Inventor: Toby Cowe, Oxfordshire (GB)

(73) Assignee: OWEN MUMFORD LIMITED, Oxfordshire (GB)

( * ) Notice: Subject to any disclaimer, the term of this patent is extended or adjusted under 35 U.S.C. 154(b) by 0 days. days.

(21) Appl. No.: 14/761,997

(22) PCT Filed: Jan. 21, 2014

(86) PCT No.: PCT/GB2014/000021
§ 371 (c)(1),
(2) Date: Jul. 20, 2015

(87) PCT Pub. No.: WO2014/111683
PCT Pub. Date: Jul. 24, 2014

(65) Prior Publication Data
US 2015/0314072 A1  Nov. 5, 2015

Related U.S. Application Data

(60) Provisional application No. 61/754,997, filed on Jan. 22, 2013.

(30) Foreign Application Priority Data

Jan. 21, 2013 (GB) .................................. 1301046.7

(51) Int. Cl.
*A61M 5/178* (2006.01)
*A61M 5/315* (2006.01)
(Continued)

(52) U.S. Cl.
CPC ........ *A61M 5/3153* (2013.01); *A61M 5/1452* (2013.01); *A61M 5/204* (2013.01);
(Continued)

(58) Field of Classification Search
CPC ........................ A61M 5/31535; A61M 5/3153
See application file for complete search history.

(56) References Cited

U.S. PATENT DOCUMENTS

| | | | | |
|---|---|---|---|---|
| 5,988,452 A | * | 11/1999 | Dent ...................... | A61M 5/204 222/309 |
| 2007/0191784 A1 | * | 8/2007 | Jacobs .............. | A61M 5/31555 604/224 |
| 2010/0036320 A1 | * | 2/2010 | Cox ................... | A61M 5/31593 604/135 |

FOREIGN PATENT DOCUMENTS

| CN | 1913932 A | 2/2007 |
|---|---|---|
| CN | 1933864 A | 3/2007 |

(Continued)

OTHER PUBLICATIONS

International Search Report, dated Jul. 21, 2014, from corresponding PCT application.
(Continued)

*Primary Examiner* — Nathan R Price
*Assistant Examiner* — John Doubrava
(74) *Attorney, Agent, or Firm* — Young & Thompson

(57) ABSTRACT

A dosing mechanism (6) for delivering a plurality of single metered doses includes a dose delivery mechanism; and a non-return mechanism (10), arranged to prevent the dose delivery mechanism from returning toward a primed position until a full metered dose has been delivered. The non-return mechanism includes a track defining an actuation path and a return path and an engagement member arranged to be received within the track. The track and engagement member are relatively moveable such that the engagement member is arranged to move along the actuation path during actuation of the dose delivery mechanism and along the return path during priming of the dose delivery mechanism. At least a portion of the actuation path is provided with a (Continued)

toothed profile to prevent reverse movement of the engagement member in the actuation path.

18 Claims, 8 Drawing Sheets

(51) Int. Cl.
*A61M 5/145* (2006.01)
*A61M 5/24* (2006.01)
*A61M 5/20* (2006.01)

(52) U.S. Cl.
CPC ............ *A61M 5/24* (2013.01); *A61M 5/3158* (2013.01); *A61M 5/31501* (2013.01); *A61M 5/31535* (2013.01); *A61M 5/31541* (2013.01); *A61M 5/31555* (2013.01); *A61M 5/31566* (2013.01)

(56) References Cited

FOREIGN PATENT DOCUMENTS

| | | |
|---|---|---|
| CN | 101370540 A | 2/2009 |
| CN | 101903059 A | 12/2010 |
| CN | 102639173 A | 8/2012 |
| WO | 9413339 | 6/1994 |
| WO | 9811926 A1 | 3/1998 |
| WO | 2005097240 | 10/2005 |
| WO | 2009080775 | 7/2009 |
| WO | 2011039210 | 4/2011 |
| WO | 2011154484 | 12/2011 |

OTHER PUBLICATIONS

Great Britain Search Report, dated Apr. 30, 2013, from corresponding GB application.

* cited by examiner

DOSING MECHANISM

FIELD OF THE INVENTION

The present invention relates to a dosing mechanism having a non-return mechanism which is arranged to prevent the mechanism from returning to a primed position until a full metered dose has been delivered. Particularly, but not exclusively, the invention relates to pen injector including such a dosing mechanism.

BACKGROUND OF THE INVENTION

Dosing mechanisms are commonly used for the delivery of metered doses of therapeutic material from a cartridge (or other reservoir). For example a dosing mechanism may be provided as part of a pen injector in which a cartridge containing therapeutic material, for example insulin, is received in (or formed by) a pen body.

Such dosing mechanisms are arranged to administer a plurality of repeatable single metered doses. The volume of each single dose may be variable and, therefore, a dose selector, for example a dial, may be provided for adjusting the action of the dosing mechanism.

A dose delivery mechanism is generally provided which expels a selected dose in response to a used pressing a release button. The dose delivery mechanism is moveable between a primed position in which it is ready to be released and an end position in which a dose has been expelled. A return spring (or other biasing means) may be provided which urge the dose delivery mechanism to its primed position. Alternatively, the dose delivery mechanism may be biased towards its end position and manual means may be provided for priming the mechanism (for example the release mechanism may be primed such that a catch holds it in position against a biasing spring and the release button may release the catch).

The applicants have now found that in some dosing mechanisms (and particularly in mechanisms that are biased towards a primed position) there is a risk that a user may pause during delivery of a medicament and allow the dosing mechanism to return (or partially return) towards its primed position. This results in a risk that an additional dose (or partial dose) may be delivered over and above the desired single metered dose.

Accordingly, embodiments of the invention seek to provide an improved dosing mechanism in which the risk of a partial dose delivery is reduced or removed.

STATEMENT OF INVENTION

According to a first aspect of the invention, there is provided a dosing mechanism for delivering a plurality of single metered doses comprising: a dose delivery mechanism; and a non-return mechanism, arranged to prevent the dose delivery mechanism from returning toward a primed position until a full metered dose has been delivered; wherein the non-return mechanism comprises:

a track defining an actuation path and a return path;

an engagement member arranged to be received within said track;

the track and engagement member being relatively moveable such that the engagement member is arranged to move along the actuation path during actuation of the dose delivery mechanism and along the return path during priming of the dose delivery mechanism; and wherein at least a portion of the actuation path is provided with a toothed profile to prevent reverse movement of the engagement member in the actuation path.

The dosing mechanism may for example be a pen injector dosing mechanism.

It will be appreciated that the dose delivery mechanism generally moves from a primed position to an end position during actuation and generally moves from the end position to the primed position during priming. The movement of the dose delivery mechanism may generally be considered to cause the relative movement of the non-return mechanism.

The relative movement between the engagement member and track may be directly coupled to the movement of the dose delivery mechanism. Embodiments of the invention are arranged such that the engagement member cannot reverse direction when in the actuation path and therefore the dose delivery mechanism can only return to the primed position when the engagement member is in the return path.

The return path and actuation path of the track may be substantially parallel. The engagement member may generally only transfer between the actuation path and return path at the end of the paths. The engagement member may only transfer between the actuation path and return path when the dosing mechanism is in its primed position or end position. Thus, it will be appreciated that the toothed profile may be arranged to ensure that the engagement member must travel along the full length of the actuation path to operate the dose delivery mechanism and subsequently pass along the return path in order to return to its primed position.

The track may further comprise first and second transverse portions which connect adjacent ends of the actuation and return paths so as to define a closed loop. A closed loop track arrangement may provide an outer bounding wall around the track which limits the range of motion of the engagement member (and therefore dose delivery mechanism). Specifically, the transverse portion arranged to transfer the engagement member from the actuation path to the return path may provide a stop for the end position of the engagement member (and therefore dose delivery mechanism). The transverse portion arranged to transfer the engagement member from the return path to the actuation path may provide a stop for the primed position of the engagement member (and therefore dose delivery mechanism).

The transverse portions may each join the actuation and return paths at an oblique angle. Thus, the transverse portions may provide an inclined transfer path for the engagement member from one of the actuation or return path to the other of said actuation path. This may ensure that the engagement member is inclined along the path towards the correct path depending upon the stage of actuation.

The engagement member and track may be relatively laterally movable. Thus, the actuation and return paths may be spaced apart (for example parallel) and the engagement member may move relative to the track to transfer from one path to the other. The lateral movement may be against a biasing means. For example, a biasing means may be arranged to bias the relative positions of the engagement member and track such that the engagement member is in a central position (i.e. a position in which it is positioned between the actuation and return paths) when no force is applied. For example, the engagement member and/or track may be bidirectional sprung.

At least a portion of the return path may also be provided with a toothed profile to prevent reverse movement of the engagement member in the return path. Thus, the non-return member may further be arranged to prevent the dose delivery mechanism from returning to an end position until it has fully returned to its primed position. Further, the return path may be arranged such that the engagement member (and therefore dose delivery mechanism) may remain in a partially primed position if there is insufficient therapeutic material available to prime the dose delivery mechanism.

The toothed profile(s) may be provided on a wall of the track (for example a side wall). The toothed profile may vary along the length of the actuation and/or return path. The variation of the profile may provide a degree of tactile feedback to a user during actuation. For example, the final tooth in the (or each path) may have a larger and/or steeper tooth profile so as to provide an audible and/or tactile indication of the end of travel.

One of the track and engagement member may be connected to the dose delivery mechanism, and the other of the track and engagement member may be connected to a housing of the dosing mechanism. The connection may be via a slidable or movable coupling.

The track may be provided on a track carrier which may be connected to (for example slidably mounted to) one of the dose delivery mechanism or a housing of the dosing mechanism. The track carrier may be a substantially annular collar. The annular collar may for example be rotatably mounted to the housing of the dosing mechanism.

The engagement member is linearly coupled to one of the dose delivery mechanism or a housing of the dosing mechanism (for example the other of said from than that of the track carrier). The engagement member may, for example, be provided on a substantially annular collar which is axially slidably coupled to one of the dose delivery mechanism or a housing of the dosing mechanism. The engagement member may provide a boss on the annular collar (and the boss may be sized and dimensioned so as to be received with the track).

The relative movement between the track and the engagement member may be rotational movement. Accordingly, the actuation and return paths may be generally circumferentially extending.

The dose delivery mechanism may be a generally linear arrangement (for example it may be linearly actuated) and therefore the dose mechanism may further comprises a cam arranged to provide relative rotational movement between the track and the engagement member in response to the linear movement of the dose delivery mechanism. For example, the cam may comprise a helical coupling. The helical coupling may, for example be arranged between the track carrier and the dose delivery mechanism (for example to rotate the track carrier (and therefore track) in response to a linear movement of the dose delivery mechanism).

According to a further embodiment of the invention, there is provided a pen injector apparatus comprising a dosing mechanism in accordance with an embodiment of the invention.

The pen injector may comprise a window for showing the position of the non-return mechanism. The window may be arranged such that the position of either the engagement member (or engagement member carrier such as the annular collar) or track (or track carrier) can be observed. For example, the window may be arranged to indicate whether the non-return mechanism is in a primed position and may therefore indicate whether the injector is ready to use or unavailable (for example as a result of being empty)

The dose delivery mechanism may be arranged to deliver a metered dose of therapeutic material from a cartridge (which may be received by or formed as part of the pen injector).

The dose delivery mechanism is arranged to cause therapeutic material to be drawn from a cartridge into a conduit by negative pressure and to subsequently discharge a metered dose from the conduit via a delivery needle. For example, the dose delivery mechanism may be substantially as described in the applicants earlier UK Patent Application GB1217765.5 (OML132; having a filing date of 4 Oct. 2012) the contents of which are incorporated herein by reference.

Thus, according to a further embodiment of the invention, there is provided a pen injector apparatus for use with a cartridge to deliver a plurality of single metered doses therefrom, the injector apparatus comprising:

a body being arranged to provide a conduit which, in use, provides a fluid communication path between the cartridge and a delivery needle; and a dose delivery mechanism arranged to expel therapeutic material from the cartridge; wherein the mechanism is arranged to draw therapeutic material from the cartridge into the conduit by negative pressure and discharge a metered dose from the conduit via said delivery needle;

wherein the injector further comprises a non-return mechanism, arranged to prevent the dose delivery mechanism from returning toward the primed position until a full metered dose has been delivered.

In a preferred embodiment the dosing mechanism is arranged to discharge the metered dose from the conduit by positive pressure.

The injector may comprise a non-return valve arranged to prevent fluid flow from the conduit to the cartridge. The injector may comprise a non-return valve arranged to prevent fluid flow from the needle to the conduit. The, or each, non-return valve may be biased to a closed position. As such a minimum pressure difference may be required to overcome the valve and enable fluid flow to or from the conduit.

The dose delivery mechanism may comprise a positive displacement pump. A positive displacement pump is a pump which displaces a known quantity of fluid with each action of its pumping element.

The non-return member may be further arranged to prevent the dose delivery mechanism from being driven toward an end position (i.e. the fully actuated position) until it has fully returned to its primed position.

Whilst the invention has been described above, it extends to any inventive combination of features set out above or in the following description or drawings.

BRIEF DESCRIPTION OF THE DRAWINGS

Specific embodiments of the invention will now be described in detail, by way of example only, and with reference to the accompanying drawings in which.

DETAILED DESCRIPTION OF EMBODIMENTS

Front as used herein will be understood to refer to the end of the pen injector assembly (or components thereof) which, in use, are closest to the delivery needle delivery end of the pen injector (i.e. the end which is pointed at the skin). Rear as used herein will be understood to refer to the end of the pen injector assembly (or components thereof) which, in use, are furthest from the delivery needle delivery end of the pen injector (i.e. the end which is pointed away from the skin). Forward and rearward will, likewise, be understood to refer to the directions orientated towards the front and rear of the pen injector assembly.

Figure 1:
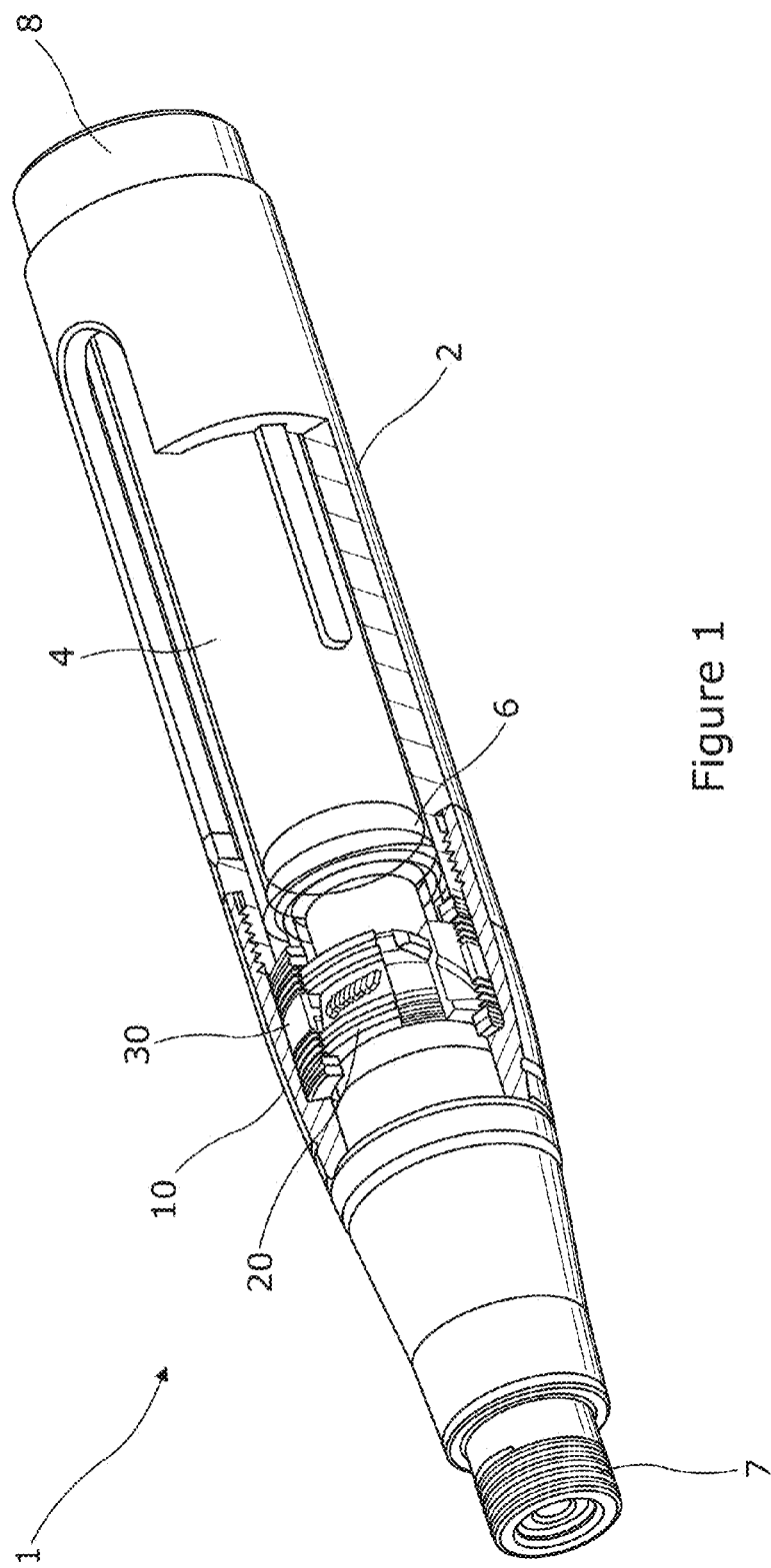
FIG. 1 is a schematic three dimensional, partial cut away, view of a pen injector according to a first embodiment of the invention.

A pen injector 1 in accordance with an embodiment of the invention is shown in FIG. 1. The injector comprises a body 2 (which is typically formed of injection moulded plastic) which is arranged to receive a cartridge 4 containing a therapeutic material (for example, insulin) to be administered. A forward end of the injector body 2 is provided, in use, with a needle for delivery of the material. Typically, the needle may be provided as a detachable needle assembly (such that the needle may be a single use item) and therefore the forward end of the pen is provided with a needle receiving portion 7 which may for example have a suitable threaded portion. The pen injector further comprises a dosing mechanism 6 which is arranged to administer a plurality of repeatable single metered doses from the cartridge 4 via a needle assembly attached to the needle receiving portion 7. The dosing mechanism 6 is actuated via an actuation button 8 provided at the rearmost end of the injector body 2.

The dosing mechanism 6 of the preferred embodiment comprises a dose delivery mechanism of the general type described in the applicants earlier UK Patent Application GB1217765.5. Therefore, a conduit (or chamber) is provided in the body 2 having a pair of non-return valves and a piston member (or other means to vary the volume in communication with the conduit or chamber). The non-return valves are respectively arranged at either side of the conduit so as to prevent reverse fluid flow from the conduit in to the cartridge 4 (the rearward valve) and to prevent reverse fluid flow from the needle to the conduit (the forward valve). The dosing mechanism 6 is actuated by being urged forwards by the actuation button 8 (and may for example be mechanically assisted by a spring means). During actuation the volume of the conduit is reduced creating a positive pressure in the conduit which acts urge the rearward non-return valve closed (and opens the forward valve) and causes a metered dose to be expelled from the injector 1. The dosing mechanism 6 is biased rearwardly such that it returns to a primed position when pressure is released from the actuation button 8. As the dosing mechanism 6 moves rearwardly, the volume of the conduit is increased resulting in a negative pressure which acts to acts urge the forward non-return valve closed (and opens the rearward valve). This results in a metered dose being drawn from the cartridge 4 into the conduit. Thus, the dosing mechanism is primed and ready to dispense a further metered dose upon the next actuation of the dosing mechanism 6.

In accordance with the invention, the injector 1 further comprises a two way non-return mechanism 10. The non-return mechanism 10 is arranged to both prevent the dose delivery mechanism from returning to the primed position until it has reached its end position (i.e. it has been fully actuated), and to prevent the dose delivery mechanism from being actuated until it has returned to the fully primed position. As best seen in FIGS. 2a to 2f, the non-return mechanism comprises a track 20 and an engagement member 30.

The engagement member 30 comprises an annular collar 33 which is provided within an annular recess 3 in the body 2 of the injector 1. The axial length of the collar 30 is less than that of the annular recess 3 such that the collar may slide axially. A pair of spring members 31 and 32 are provided between the annular recess 3 and collar 30 such that the collar is bidirectionally sprung and biased towards a central axial position within the recess 3. The engagement member 30 further comprises an inwardly radially projecting boss 34. As will be described below, the boss 34 is sized and dimensioned for cooperation with the track 20.

The track 20 comprises a track carrier 22, in the form of an annular collar, which is coupled to the dose delivery mechanism by a helical coupling 40. The coupling 40 is received within a cooperating helical groove 42 on the inner surface of the track carrier 22. The carrier 22 is typically mounted on thrust washers/bearings so as to reduce or avoid undesirable interaction forces in use. The outer surface of the track carrier 22 has an outer wall 27 which surrounds, and is spaced apart from, a toothed central ridge member 26 so as to define a closed loop track. The track comprises an actuation path 24 and a return path 25 each of which are substantially parallel and extend in a substantially circumferential direction. The toothed central ridge member 26 is provided with angled teeth on both the actuation path side and return path side (with the teeth having opposite angles to provide a ratchet type arrangement in both paths). The adjacent ends of the paths 24 and 25 are connected by transverse track portions 28 and 29.

The operation of the non-return mechanism 10 will now be described in further detail with reference to FIGS. 2a to 2f which show the actuation sequence of the mechanism.

Figure 2A:
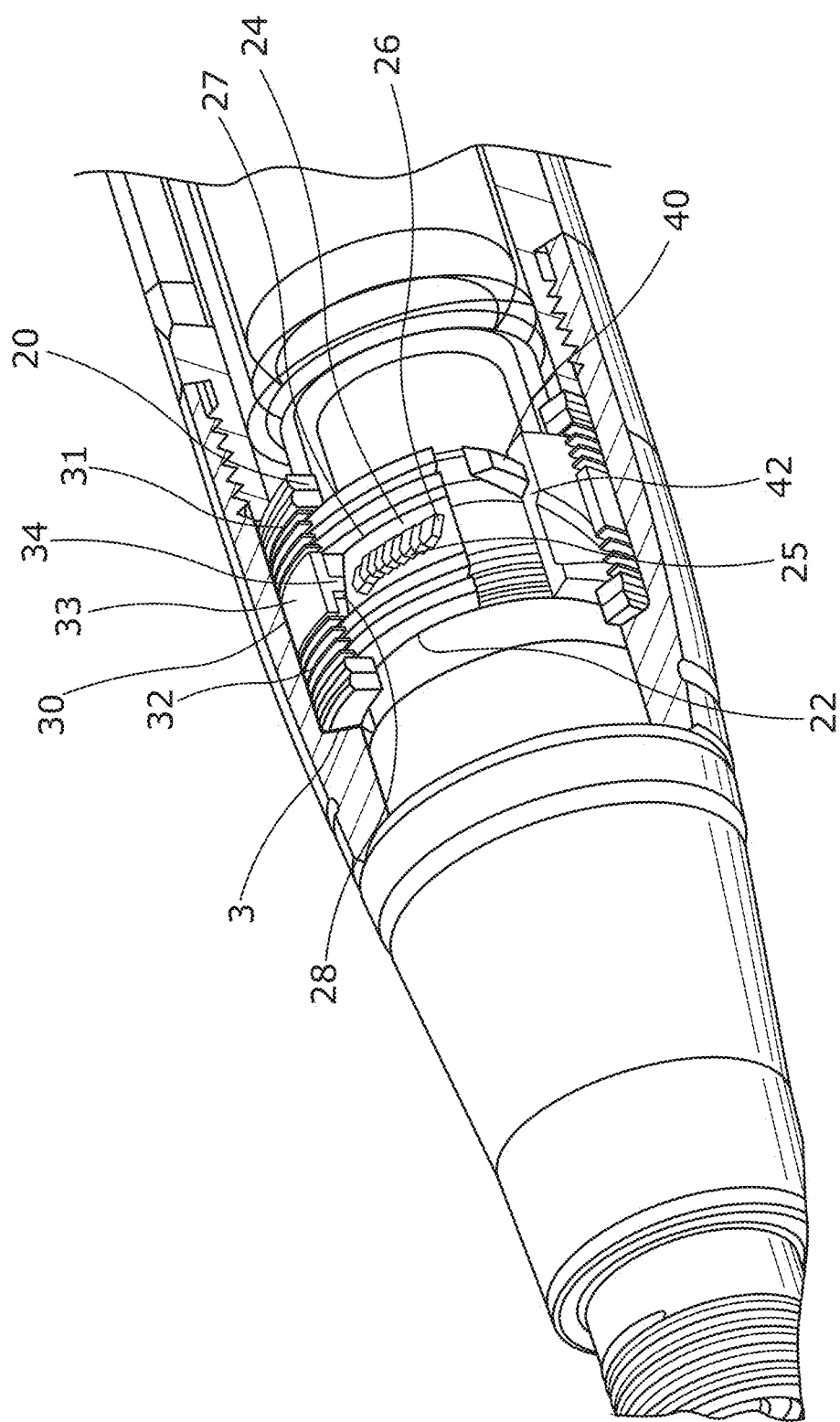
FIGS. 2a to 2f are schematic three dimensional, partial cut away, view of a detail of the pen injector of FIG. 1 in use.
Figure 2B:
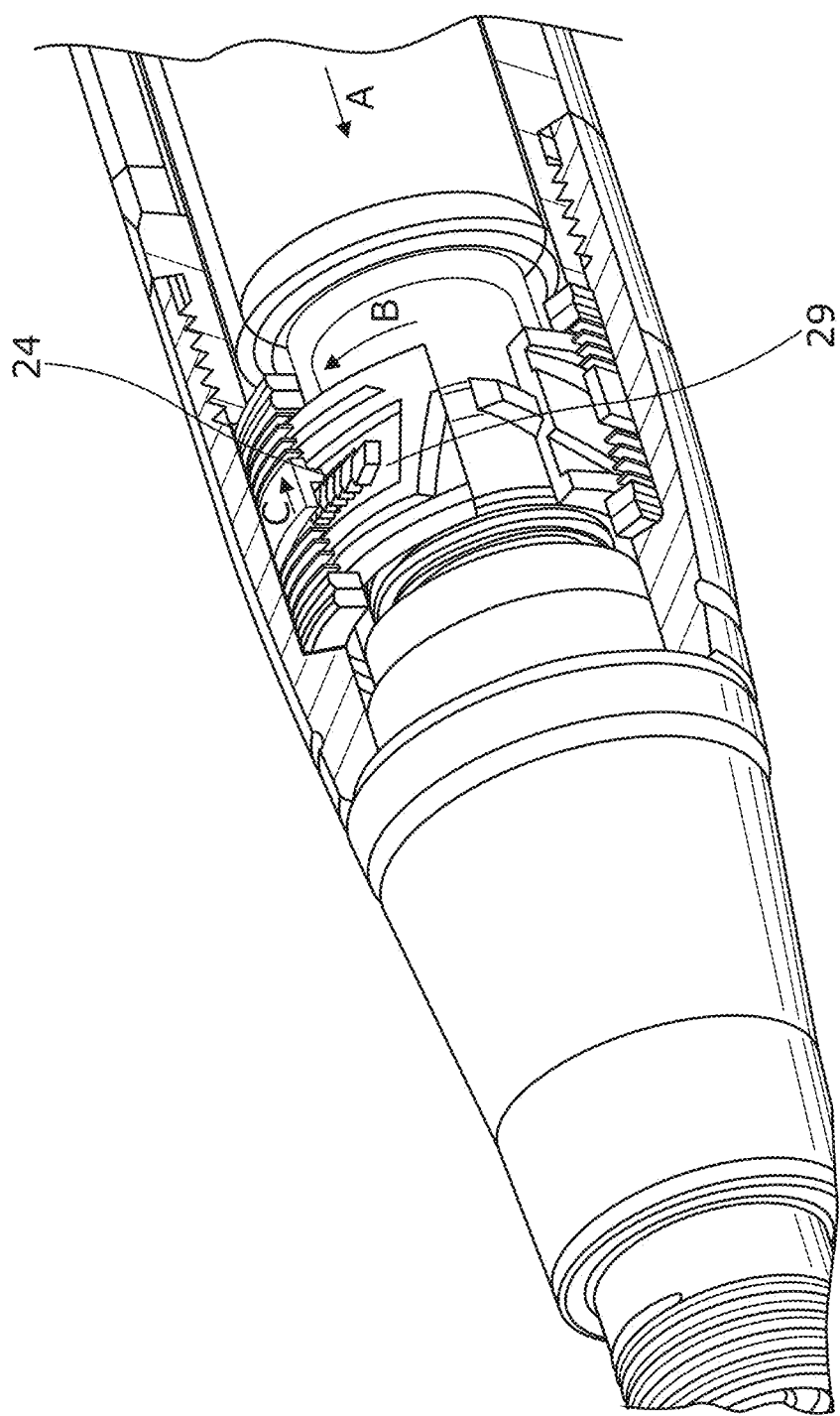
Figure 2C:
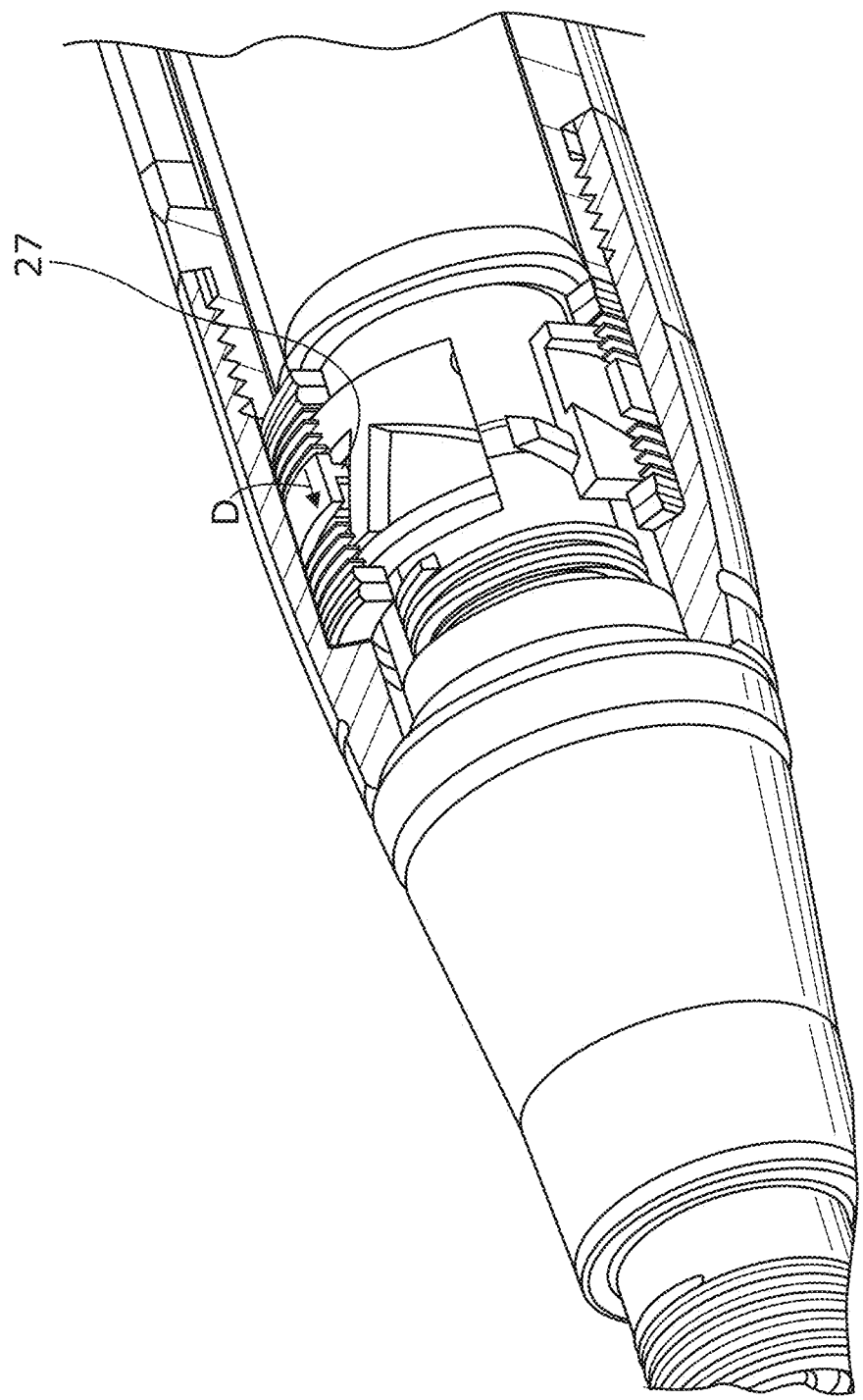

Prior to depression of the actuation button 8 the dose delivery mechanism is in the position shown in FIG. 2a. The boss 34 of the engagement member 30 is positioned within the first transverse portion 28, which it will be noted defines an inclined track portion so as to direct the boss 34 towards the actuation track 24.

As the actuation button 8 is depressed, the dose delivery mechanism moves forwards within the body 2 of the injector (typically along with the cartridge 4). This forward movement (in the direction of arrow A) results in rotational movement of the track 20 (in the direction of arrow B) as a result of the interconnection between the helical coupling 40 and the helical groove 42. The resulting relative movement between the track 20 and the engagement member 30 causes the boss 34 to enter the actuation path 24. As a result, the engagement member 30 cams rearwards compressing the first spring 31.

In the event that pressure is removed from the actuation button 8 in this position the boss 34 will be engaged by angled teeth of the central ridge member 26 (towards which it will be biased by the springs 31 and 32). Thus, it is not possible for the boss 34 of the engagement member to travel the reverse direction along the actuation path 24. This prevents reverse rotation of the track 20, and, therefore, the dose delivery mechanism cannot return towards its pre-actuation position (i.e. the primed position of FIG. 2a).

The final tooth of the central ridge member 26 has a slightly steeper and larger profile than the other teeth. Therefore, at the end of the actuation the user will be provided with tactile and audible feedback that travel has completed. At this point, the mechanism will reach the end position shown in FIG. 2c. In this position, the boss 26 is disposed within the second transverse portion 28. The outer wall 27 of the track provides a stop to delimit the travel of the non-return mechanism (and therefore the dosing mechanism). The springs 31 and 32 serve to move the engagement member 30 forwards (in the direction of arrow D) such that the boss 34 is centrally located in the transverse portion 28.

Figure 2D:
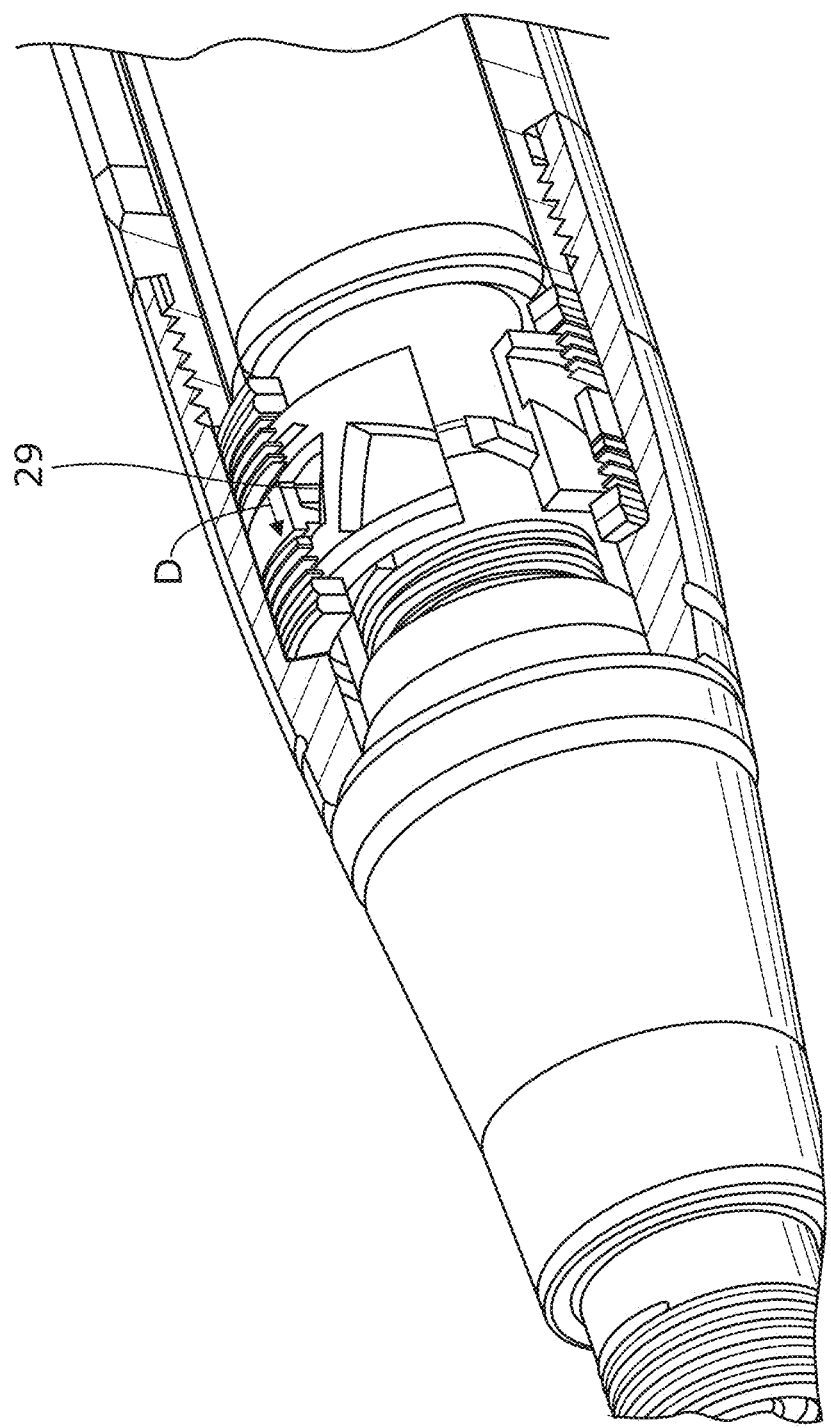
Figure 2E:
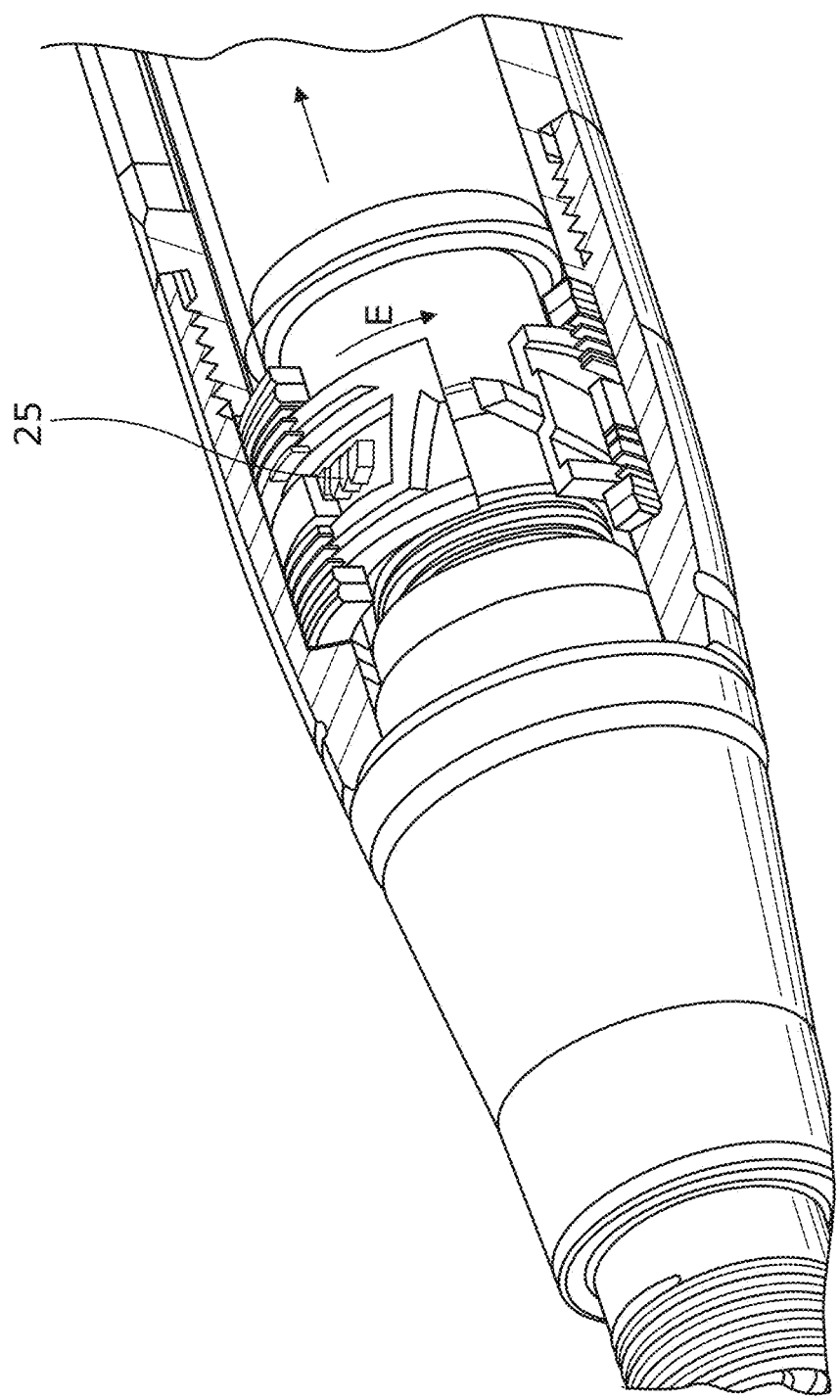

Again the transverse portion 28 is inclined (and is generally parallel to the first transverse portion so as to direct the boss 34 towards the return path 24 when it commences its return travel, as shown in FIG. 2d. Thus, the engagement member 30 cams forward as return travel of the dose delivery mechanism commences.

As the dose delivery mechanism returns to its (rearward) primed position (typically under the load of a return spring) the helical coupling 40 and helical groove 42 provide a resulting rotational movement of the track 20 in the opposite direction to the actuation rotation (in the direction of arrow E). Thus, the boss 34 travels along the return path 24.

If a user attempts to re-actuate the dosing mechanism while the non-return mechanism 10 is in this configuration the boss 34 will be engaged by the angled teeth of the central ridge member 26 (towards which it will be biased by the springs 31 and 32). Thus, it is not possible for the boss 34 of the engagement member to travel the reverse direction along the return path 24. This prevents forward rotation of the track 20, and, therefore, the dose delivery mechanism during priming. As such, the dose delivery mechanism is prevented from being urged directly towards its end position (i.e. the position of FIG. 2d).

Additionally, in the event that there is insufficient therapeutic material remaining in the cartridge 4 to fully prime the dose delivery mechanism the non-return mechanism 10 will result hold the mechanism in its partially returned position. This is advantageous in that it will provide the used with an indication that the cartridge requires replenishment or replacement. This advantage may be further utilised by providing a window in the injector body 2 such that the collar of the engagement member 30 is visible only in the forward position of FIG. 2d. Thus, in normal operation the collar is only transiently visible whereas in the event of the cartridge running out the collar will be held in alignment with the window.

Figure 2F:
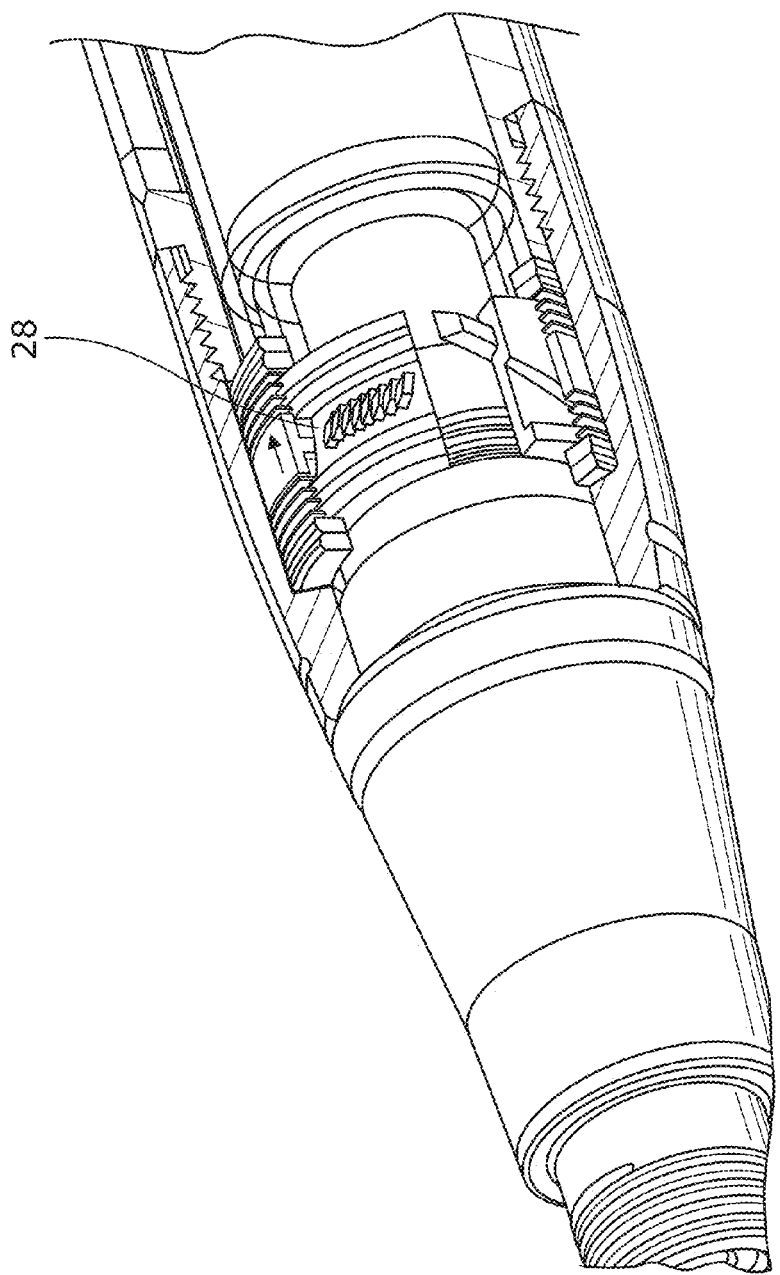

Once the dose delivery mechanism is fully primed the mechanism will reach the position shown in FIG. 2f. In this position, the boss 26 has returned to the first transverse portion 28. The outer wall 27 of the track provides a stop to delimit the travel of the non-return mechanism (and therefore the dosing mechanism). The springs 31 and 32 serve to move the engagement member 30 forwards (in the direction of arrow D) such that the boss 34 is centrally located in the transverse portion 28.

Figure 3:
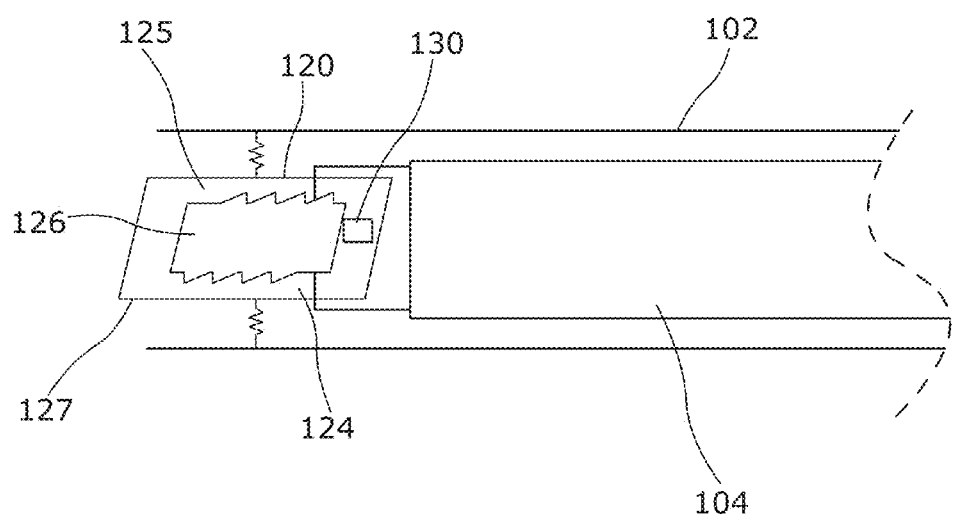
FIG. 3 is a schematic representation of an alternative embodiment of the invention.

An alternative embodiment is shown schematically in FIG. 3. The operating principle of this embodiment is identical to that of the preceding embodiment but the relative movement between the track 120 and the engagement member 130 is linear rather than rotational. The track comprises parallel axially aligned actuation 124 and return paths 126 and is defined by an outer wall 127 and a toothed central portion 127 arranged to provide a ratchet mechanism in each path. This arrangement provides a simplified mechanical arrangement but results in a less compact non-return mechanism. Furthermore, it will be appreciated that the rotational cam action of the earlier embodiment provides a mechanical advantage which is not provided in the simplified embodiment illustrated in FIG. 3.

It will further be noted that in this embodiment the arrangement of the engagement member 130 and track 120 have been effectively reversed (and the skilled person will appreciate that the arrangement could also be reversed in the embodiment of FIG. 2 without altering the function of the invention). Thus, in this embodiment the track member 120 is coupled to the body 102 while the engagement member 130 is coupled to the dosing mechanism. Additionally, it may be noted that the track member 120 is bi-directionally sprung in this embodiment (rather than the engagement member 130); again the skilled person will appreciated that this could be reversed in either of the embodiments.

It will be appreciated that the term cartridge as used herein is intended to refer to any suitable container for containing therapeutic material in a pen injector. The cartridge could, for example, include a syringe. In alternate embodiments the cartridge could be integrally formed with or by a portion of the pen injector (for example the injector body or housing).

Although the invention has been described above with reference to one or more preferred embodiments, it will be appreciated that various changes or modifications may be made without departing from the scope of the invention as defined in the appended claims.

The invention claimed is:

1. A pen injector apparatus, that includes a dosing mechanism, for delivering a plurality of single metered doses, the dosing mechanism of the pen injector apparatus comprising:
   a linearly actuated dose delivery mechanism arranged to deliver a metered dose of therapeutic material from a cartridge;
   a non-return mechanism, arranged to prevent the dose delivery mechanism from returning toward a primed position until a full metered dose has been delivered, the non-return mechanism including
      a track defining an actuation path and a return path, and
      an engagement member arranged to be received within said track,
         the track and engagement member being relatively rotationally moveable such that the engagement member is arranged to move along the actuation path during actuation of the dose delivery mechanism and along the return path during priming of the dose delivery mechanism, and
         at least a portion of the actuation path being provided with a toothed profile to prevent reverse movement of the engagement member in the actuation path; and
   a cam arranged to provide relative rotational movement between the track and the engagement member in response to a linear movement of the dose delivery mechanism.

2. The pen injector apparatus of claim 1, wherein the actuation and return paths are parallel.

3. The pen injector apparatus of claim 1, wherein the track further comprises first and second transverse portions which connect adjacent ends of the actuation and return paths so as to define a closed loop.

4. The pen injector apparatus of claim 3, wherein the transverse portions join the actuation and return paths at an oblique angle.

5. The pen injector apparatus of claim 1, wherein the engagement member and track are relatively laterally movable.

6. The pen injector apparatus of claim 5, wherein relative lateral movement is against a biasing means.

7. The pen injector apparatus of claim 6, wherein the biasing means is arranged to bias the engagement member to a central position in which the engagement member is positioned between the actuation and return paths.

8. The pen injector apparatus of claim 1, wherein at least a portion of the return path is provided with a toothed profile to prevent reverse movement of the engagement member in the return path.

9. The pen injector apparatus of claim 1, wherein the toothed profile is provided on a side wall of the track.

10. The pen injector apparatus of claim 1, wherein the toothed profile is varied along the length of the actuation mechanism so as to provide a tactile feedback during actuation.

11. The pen injector apparatus of claim 1, wherein one of the track and engagement member is connected to the dose delivery mechanism, and the other of the track and engagement member is connected to a housing of the dosing mechanism.

12. The pen injector apparatus of claim 11, wherein the track is provided on a track carrier which is connected to one of the dose delivery mechanism or a housing of the dosing mechanism.

13. The pen injector apparatus of claim 12, wherein the track carrier comprises an annular collar.

14. The pen injector apparatus of claim 11, wherein the engagement member is linearly coupled to one of the dose delivery mechanism or a housing of the dosing mechanism.

15. The pen injector apparatus of claim 1, wherein the actuation and return paths are circumferentially extending.

16. The pen injector apparatus of claim 1, wherein the cam comprises a helical coupling.

17. The pen injector apparatus of claim 1, further comprising:
   a window for showing the position of the non-return mechanism.

18. The pen injector apparatus of claim 1, wherein the dose delivery mechanism is arranged to deliver a metered dose of therapeutic material from a cartridge.

* * * * *